United States Patent
Charo et al.

(10) Patent No.: US 9,061,058 B2
(45) Date of Patent: Jun. 23, 2015

(54) USE OF POL III PROMOTERS FOR CONTROLLED EXPRESSION OF THERAPEUTIC PROTEINS

(75) Inventors: Jehad Charo, Berlin (DE); Thomas Blankenstein, Berlin (DE)

(73) Assignee: MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 1397 days.

(21) Appl. No.: 12/293,606

(22) PCT Filed: Mar. 20, 2007

(86) PCT No.: PCT/EP2007/002605
§ 371 (c)(1),
(2), (4) Date: Mar. 10, 2010

(87) PCT Pub. No.: WO2007/107380
PCT Pub. Date: Sep. 27, 2007

(65) Prior Publication Data
US 2010/0160416 A1    Jun. 24, 2010

(30) Foreign Application Priority Data

Mar. 20, 2006 (EP) .................................... 06005683
Oct. 2, 2006 (EP) .................................... 06076822

(51) Int. Cl.
*C07H 21/02* (2006.01)
*A61K 48/00* (2006.01)

(52) U.S. Cl.
CPC ........ *A61K 48/0066* (2013.01); *C12N 2799/027* (2013.01); *C12N 2830/85* (2013.01)

(58) Field of Classification Search
USPC ....................................... 536/23.1; 514/44 R
See application file for complete search history.

(56) References Cited

U.S. PATENT DOCUMENTS 5,618,717 A * 4/1997 Wei et al. .................... 435/325

FOREIGN PATENT DOCUMENTS

WO    03/023015 A2    3/2003
WO    2005/073380 A2    8/2005

OTHER PUBLICATIONS

Gunnery et al., 1995, Molecular and Cellular Biology, 15: 3597-3607.*
Brummelkamp et al., 2002, Cancer Cell, 2: 243-247.*
Mitchell et al., 1992, The Journal of Biological Chemistry, 267: 1905-2005.*
Teichmann et al., 2010, Transcription, 1: 130-135.*
Dohjima et al., 2003, Molecular Therapy, 7: 811-816.*
Braglia et al. Journal of Biological Chemistry 280(20):19551-19562, 2005.*
Geiduscheck and Kassavetis. JMB 310:1-26, 2001.*
Shul Zhenko, V. N. et al: "Cloning of human ApoAl gene and its expression in murine fibroblasts" in Database CA [Online] Chemical Abstracts Service, Columbus, Ohio, US; retrieved from STN Database accession No. 1990:31666, & Biopolimery I Kletka (1985-2000), 5(5), 105-7 CODEN: BIKLEK.
Mital et al., RNA Polymerase III Transcription from the Human U6 and Adenovirus Type 2 VAI Promoters Has Different Requirements for Human BRF, a Subunit of Human TFIIIB, Molecular and Cellular Biology, Dec. 1996, p. 7031-7042.

* cited by examiner

*Primary Examiner* — Marcia S Noble
(74) *Attorney, Agent, or Firm* — Joyce von Natzmer; Agris & von Natzmer LLP

(57) ABSTRACT

The present invention relates generally to the field of molecular biology. More specifically, the present invention relates to expression systems for use in modulating the expression of protein coding target genes in vivo or in vitro. More specific, this invention relates to RNA polymerase III-based methods and systems for expression of therapeutic proteins in cells in vivo or in vitro.

8 Claims, No Drawings

USE OF POL III PROMOTERS FOR CONTROLLED EXPRESSION OF THERAPEUTIC PROTEINS

This is the U.S. national stage of International application PCT/EP2007/002605, filed Mar. 20, 2007 designating the United States.

The present invention relates generally to the field of molecular biology. More specifically, the present invention relates to expression systems for use in modulating the expression of protein coding target genes in vivo or in vitro. More specific, this invention relates to RNA polymerase III-based methods and systems for expression of therapeutic proteins in cells in vivo or in vitro.

Controlled protein production is a requirement for various types of therapeutic or preventive gene transfer. The major safety issue related to applications such as DNA vaccination or gene therapy is insertional oncogenesis. Having been considered for long time as a mere theoretical risk, insertional oncogenesis was recently realized as a serious adverse event that lead to the development of lymphoma in patients after receiving gene therapy. This has sparked concerted research efforts to find out a solution for this problem, namely building new constructs that can be used for gene therapy with minimized oncogenecity potential. To achieve this, efforts are being concentrated on the followings:
1. Building constructs with integrated suicide genes.
2. Deleting the U3 region of the vector LTR which results in a self-inactivating retrovirus and using internal pol II promoter to drive gene expression.
3. Utilizing tissue specific internal pol II promoters.
4. Using drug inducible promoters such as that of the Tet-regulated system.

Additional approaches are being suggested such as introducing enhancer blocking elements (insulators) to the retrovirus but their applicability to retrovirus constructs, the most promising vectors in gene therapy, are questionable.

Genes, which are carried on chromosomes, are the basic physical and functional units of heredity. Genes are specific sequences of bases that encode instructions on how to make proteins. Although genes get a lot of attention, it's the proteins that perform most life functions and even make up the majority of cellular structures. When genes are altered so that the encoded proteins are unable to carry out their normal functions, genetic disorders can result.

Gene therapy is a technique for correcting defective genes responsible for disease development, or to introduce beneficial genes to cells or organisms. Researchers may use one of several approaches for correcting faulty genes:
A normal gene may be inserted into a nonspecific location within the genome to replace a nonfunctional gene. This approach is most common.
An abnormal gene could be swapped for a normal gene through homologous recombination.
The abnormal gene could be repaired through selective reverse mutation, which returns the gene to its normal function.
The regulation (the degree to which a gene is turned on or off) of a particular gene could be altered.

In most gene therapy studies, a "normal" gene is inserted into the genome to replace an "abnormal," disease-causing gene. A carrier molecule called a vector must be used to deliver the therapeutic gene to the patient's target cells. Currently, the most common vector is a virus that has been genetically altered to carry normal human DNA. Viruses have evolved a way of encapsulating and delivering their genes to human cells in a pathogenic manner. Scientists have tried to take advantage of this capability and manipulate the virus genome to remove disease-causing genes and insert therapeutic genes.

Target cells such as the patient's liver, bone marrow, T stem- or lung cells are infected with the viral vector. The vector then unloads its genetic material containing the therapeutic human gene into the target cell. The generation of a functional protein product from the therapeutic gene restores the target cell to a normal state.

Some of the different types of viruses used as gene therapy vectors:
Retroviruses—A class of viruses that can create double-stranded DNA copies of their RNA genomes. These copies of its genome can be integrated into the chromosomes of host cells. Human immunodeficiency virus (HIV) is a retrovirus.
Adenoviruses—A class of viruses with double-stranded DNA genomes that cause respiratory, intestinal, and eye infections in humans. The virus that causes the common cold is an adenovirus.
Adeno-associated viruses—A class of small, single-stranded DNA viruses that can insert their genetic material at a specific site on chromosome 19.
Herpes simplex viruses—A class of double-stranded DNA viruses that infect a particular cell type, neurons. Herpes simplex virus type 1 is a common human pathogen that causes cold sores.

Besides virus-mediated gene-delivery systems, there are several nonviral options for gene delivery. The simplest method is the direct introduction of therapeutic DNA into target cells. This approach is limited in its application because it can be used only with certain tissues and requires large amounts of DNA.

Another nonviral approach involves the creation of an artificial lipid sphere with an aqueous core. This liposome, which carries the therapeutic DNA, is capable of passing the DNA through the target cell's membrane.

Therapeutic DNA also can get inside target cells by chemically linking the DNA to a molecule that will bind to special cell receptors. Once bound to these receptors, the therapeutic DNA constructs are engulfed by the cell membrane and passed into the interior of the target cell. This delivery system tends to be less effective than other options.

Within the framework of gene therapy, viral vectors are well known as being efficient vehicles for the stable introduction of genes into human cells. The integration of the gene which is to be introduced occurs at points of the genome chosen at random and by means of well defined insertion sequences (so-called LTRs—"long terminal repeat"). The insertion cassettes carry the gene which is to be introduced and which is expressed under the control of RNAPol II promoters, according to the biologic systems. Clinical studies with SCID-X1 patients (sever combined immunodeficiency type X1) showed that the random insertion of the vectors into the genome can lead to an unwished activation of adjacent genes including protooncogenes, which results in malign diseases, in the present case in leukemia. A great number of different—although to date unsuccessful—efforts have been made ever since to optimize such viral vectors.

The expression of proteins in eucaryotes occurs through a complex system of RNA and protein factors which catalyze in a very strictly ordered way both the transcription of genomic DNA to mRNA and the translation of mRNA to proteins. Moreover, the single steps of the gene expression take place in different compartments of the cell.

The cell is equipped with separate expression systems for the expression of RNAs which are not (!) translated to proteins. Especially responsible for this are the RNA polymerases (RNAPol) I and III. The RNAPol II transcribes the mRNA which is fundamental for protein expression.

The functional distribution to different RNA polymerases is generally very strictly regulated.

The RNA polymerase III (pol III) promoter is one found in DNA encoding 5S, U6, adenovirus VA1, Vault, telomerase RNA, tRNA genes, etc., and is transcribed by RNA polymerase III (for a review see Geiduschek and Tocchini-Valentini, 1988 Annu. Rev. Biochem. 57, 873-914; Willis, 1993 Eur. J. Biochem. 212, 1-11). There are three major types of pol III promoters: types 1, 2 and 3 (Geiduschek and Tocchini-Valentini, 1988 supra; Willis, 1993 supra). Type 1 pol III promoter consists of three cis-acting sequence elements downstream of the transcriptional start site a) 5' sequence element; b) an intermediate sequence element; c) 3' sequence element. 5S ribosomal RNA genes are transcribed using the type 1 pol III promoter (Specht et al., 1991 Nucleic Acids Res. 19, 2189-2191).

Eukaryotic nuclear gene expression is performed by three molecular complexes. These complexes are referred to as RNA polymerases (pol) I, II and III. Pol I transcribes the rRNA genes. Pol II transcribes the protein-encoding genes and many small nuclear RNA genes. Pol III, which is subdivided into three types, transcribes many untranslated gene products that are involved in RNA processing including 5S rRNA, tRNA, 06 RNA and H1 RNA molecules. Type I and II pol III promoters require intragenic sequence elements (downstream of +1) to transcribe 5S rRNA and tRNA respectively. Type III pol III promoters requires no intragenic sequence elements for transcribing their genes. Pol III promoters transcribe short RNA that rarely exceed 300 nucleotides (nt) in length all of these transcripts terminates tightly once a run of 5 or more thymidines (T) is present. Type III Pol III promoters are now used for expressing short inhibitory RNA (siRNA) for the purpose of RNA interference. Variations of this type of construct are available in which siRNA molecules are expressed from plasmid, adenoviral or retroviral back-bones. It was earlier reported that functional mRNA can be generated by RNA pol III type II promoter. They have mutated and modified the coding sequence of the 86 amino acid (aa) long HIV Tat and integrated it into the type II pol III promoter-gene VA $RNA_I$ from adenovirus type 2.

Prior art discloses expression constructs using RNA Pol III promoters used in the context of gene silencing. In spite of this disclosure, it was generally assumed that the expression and the transcriptional termination of genes through Pol III promoters is not possible.

It was therefore utterly surprising that Pol III promoters can be used for the expression of genes and for the transcriptional termination of genes in gene therapy. According to the invention, a construct was designed in which protein production is driven by type III pol III promoters. With the invention, it was shown for the first time that this type can drive protein expression in plasmid and retroviral constructs. It was also shown that, unlike expression driven by pol II promoters, protein expression driven by this type of promoters can be used to express one gene with minimal expression of its neighboring genes. In striking contrast to Pol II, Pol III can recognize termination site accurately and efficiently. This termination site is a simple cluster of four or more T residues. This signal is recognized by Pol III in the apparent absence of other factors. It has been proposed that the La autoantigen is involved in termination by Pol III. Subunits C37 and C53 of Pol III are required for the termination as Pol III lacking these subunits is deffective in transcription termination unless the heterodimer C37-053 is added.

This type of constructs wherein protein expression is driven by a Pol III promoter should prove useful for, among others, gene therapy and DNA vaccination approaches wherein only the expression of the introduced gene is desired, while the potential de novo expression from down or upstream sequences driven by the internal promoter is very limited.

The construct according to the invention allows a stable expression of any proteins, within the framework of gene therapy. The inventors presume that no unwished for activation of other genes should occur, since the RNAPol III-dependent expression can be controlled, preferably terminated, very strictly. Our data as well as several publications reporting on the transcription by Pol III promoters show that termination is efficient (See Refs: Braglia P, Percudani R, Dieci G.

Sequence context effects on oligo(dT) termination signal recognition by Saccharomyces cerevisiae RNA polymerase III. J Biol Chem. 2005 May 20; 280(20):19551-62. White R J. RNA polymerases I and III, growth control and cancer. Nat Rev Mol Cell Biol. 2005 January; 6(1):69-78. White R J. RNA polymerase III transcription and cancer. Oncogene. 2004 Apr. 19; 23(18):3208-16. Huang Y, Maraia R J. Comparison of the RNA polymerase III transcription machinery in *Schizosaccharomyces pombe, Saccharomyces cerevisiae* and human. Nucleic Acids Res. 2001 July; 29(13):2675-90. Hamada M, Sakulich A L, Koduru S B, Maraia R J. Transcription termination by RNA polymerase III in fission yeast. A genetic and biochemically tractable model system. J Biol Chem. 2000 Sep. 15; 275(37):29076-81. Paule M R, White R J. Survey and summary: transcription by RNA polymerases I and III. Nucleic Acids Res. 2000 Mar. 15; 28(6):1283-98). The invention therefore constitutes the basis for the development of safe vectors for the means of gene therapy.

The invention therefore relates to a gene therapy-construct for the expression and/or transcriptional termination of genes comprising a RNA pol III dependent promoter sequence.

Even in the light of the prior art, which as the case may be suggests the use of RNA pol III promoters in the context of gene-silencing, it was surprising that the construct according to the invention may be used for the expression and/or transcriptional termination of protein coding genes. This construct, but also the use of the construct, bears a great number of advantages for gene therapy. It provides a secure strategy for gene expression, which avoids the risk of inducing the expression of undesired genes and limits the expression to the gene of interest. The invention offers further advantages:
  departure from the beaten track
  a new perception of the problem
  satisfaction of a long-felt need or want
  hitherto all efforts of experts were in vain
  the simplicity of a solution proves inventive action, especially if it replaces a more complex doctrine
  the development of scientific technology followed another direction
  the achievement forwards the development
  misconceptions about the solution of the according problem (prejudice)
  technical progress, such as: improvement, increased performance, price-reduction, saving of time, material, work steps, costs or resources that are difficult to obtain, improved reliability, remedy of defects, improved quality, no maintenance, increased efficiency, better yield, augmentation of technical possibilities, provision of another product, opening of a second way, opening of a new field, first solution for a task, spare product, alternatives, possibility of rationalisation, automation or miniaturisation or enrichment of the pharmaceutical fund special choice (since a certain possibility, the result of which was unforeseeable, was chosen among a great number of possibilities, it is a patentable lucky choice)

error in a citation young field of technology combined invention; a combination of a number of known elements, with a surprising effect licensing praise of experts and commercial success.

The present invention solves the problem of the uncontrolled expression, preferably the uncontrolled expression attributed to pol II promoters, by providing a gene therapy construct for the expression and/or transcriptional termination of genes comprising a RNA pol III dependent promoter sequence.

In a preferred embodiment, the construct of the invention comprising at least one RNA pol III dependent promoter sequence is operably linked to at least one polynucleotide sequence of interest. This polynucleotide sequence should be devoid of long runs (usually ≥4) of T residues which can, otherwise, be modified by introducing Synonymous (silent) mutations. Similar mutagenesis was done to the hRluc sequence using oligos listed in table 1. One skilled in the art will recognize that the selection of the promoter to express the gene of interest will depend on the vector, the nucleic acid cassette, the cell type to be targeted, and the desired biological effect. One skilled in the art will also recognize that in the selection of a promoter the parameters can include: achieving sufficiently high levels of gene expression to achieve a physiological effect; maintaining a critical level of gene expression; achieving temporal regulation of gene expression; achieving cell type specific expression; achieving pharmacological, endocrine, paracrine, or autocrine regulation of gene expression; and preventing inappropriate or undesirable levels of expression. Any given set of selection requirements will depend on the conditions but can be readily determined once the specific requirements are determined. In one embodiment of the invention, the promoter is cell specific such that gene expression is restricted to red blood cells. Erythrocyte-specific expression is achieved by using the human .beta.-globin promoter region and locus control region (LCR).

Standard techniques for the construction of expression vectors suitable for use in the present invention are well-known to those of ordinary skill in the art and can be found in such publications as Sambrook et al. (1989) Molecular Cloning: A Laboratory Manual, 2nd Ed. Cold Spring Harbor, N.Y. A variety of strategies are available for ligating fragments of DNA, the choice of which depends on the nature of the termini of the DNA fragments and which choices can be readily made by the skilled artisan.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. A coding sequence (e.g. polythymidin sequence) is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

Sequences of pol III related promoters encode either constitutive or inducible promoters. The promoters may be either naturally occurring promoters or hybrid promoters. Hybrid promoters, which combine elements of more than one promoter, are also known in the art, and are useful in the present invention. It is operably linked to a nucleic acid encoding the above defined fusion polypeptide. Such linkage comprises positioning of the promoter with respect to the translation initiation codon of the nucleic acid encoding the fusion nucleic acid. The promoter sequence contains transcription and translation control sequences which mediate the expression of the fusion nucleic acid.

Pol II and Pol III transcribe substrates and recognize promoters with very different structures. They are both located in the nucleoplasm but differ in chromatographic behavior (the two elute in different fractions and salt concentration), salt requirements, subunit composition (12 for Pol II and 17 for Pol III), sensitivity to the toxin α-amanitin, and the class of RNA they synthesize. Pol II transcription is strongly inhibited by 1 μg α-amanitin while Pol III requires very high concentrations (≥10 μg) of α-amanitin to be inhibited. The most similar promoters recognized by Pol II and Pol III are U2 and U6 respectively with a major difference that is the TATA box included within the U6 which is essential for the Pol III activity. Transcripts by both polymerases can be post transcriptionally modified. Pol II transcripts are caped (7-methylguanylate attached by a triphosphate linkage to the ribose at the 5' end of the mRNA), polyaenylated (poly A tail is added at the 3'end), spliced (removes introns and attach exons) and edited by various mechanisms such as deamination. Pol III transcripts can be modified by cleavage of the 5' leader sequence, splicing to remove introns, replacement of the 3"-terminal sequences, and modification of several bases, but unlike Pol II transcripts does not require capping or polyadenylation. Promoters recognized by Pol II include: Protein coding genes, U1, U2, U4, and U5 snRNAs. Promoters recognized by Pol III include: tRNAs, 5sRNA, U6 snRNA.

Genetic material comprising nucleic acids, polynucleotides, RNA and DNA, of either natural or synthetic origin, including recombinant RNA and DNA and antisense RNA and DNA; hammerhead RNA, ribozymes, antigene nucleic acids, both single and double stranded RNA and DNA and analogs thereof, either in combination or not with other elements such as, for example, without limitation, tissue specific enhancers, and nuclear localization signals, can be introduced into eukaryotic cells or organisms/patients via transformation or transfection techniques. The present invention provides a "nucleic acid construct" or alternatively a "nucleotide construct" or alternatively a "DNA construct". The term "construct" is used herein to describe a molecule, such as a polynucleotide may optionally be chemically bonded to one or more additional molecular moieties, such as a vector, or parts of a vector. In a specific—but by no means limiting—aspect, a nucleotide construct is exemplified by a DNA expression constructs suitable for the transformation of a host cell. As used herein, the terms "transformation" and "transfection" are intended to refer to a variety of art-recognized techniques for introducing foreign nucleic acid into a host cell/or tissue, including, for example, without limitation, calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die). In order to obtain an efficient in vivo transfer of the bioactive therapeutic compositions of the present invention, various transfection agents are employed. Representative examples of transfection agents which are suitable for use with the methods of the present invention include, without limitation, calcium phosphate or calcium chloride co-precipitation, DEAE-dextran-mediated transfection, quaternary ammonium amphiphile DOTMA ((dioleoyloxypropyl)trimethylammonium bromide). Lipophilic glutamate diesters with pendent trimethylammonium heads; the metabolizable parent lipids such as the cationic lipid dioctadecylamido glycylspermine (DOGS) and dipalmitoylphosphatidyl ethanolamylspermine (DPPES); metabolizable quaternary ammonium salts (DOTB, N-(1-[2,3-dioleoyloxy]propyl)-N,N,N-trimethylammonium methylsulfate (DOTAP), polyethyleneimine (PEI), dioleoyl esters, ChoTB, ChoSC, DOSC); 3beta[N—(N',N'-dimethylaminoethane)carbamoyl]cholesterol (DC-Chol), dioleoylphosphatidyl ethanolamine (DOPE)/3beta[N—(N',N'-dimethylaminoethane)carbamoyl]cholesterolDC-Chol in one to one mixtures, spermine, spermidine, lipopolyamines, lipophilic polylysines (LPLL), [[(1,1,3,3-tetramethylbutyl)cresoxy]ethoxy]ethyl]dimethylbenzylamionium hydroxide (DEBDA hydroxide) with excess phosphatidylcholine/cholesterol, cetyltrimethylammonium bromide (CTAB)/DOPE mixtures, lipophilic diester of glutamic acid (TMAG) with DOPE, CTAB, DEBDA, didodecylammonium bromide (DDAB), and stearylamine in admixture with phosphatidylethanolamine, DDAB/DOPE (TransfectACE, GIBCO BRL), and oligogalactose bearing lipids. Also encompassed within the present invention is the use of various transfection enhancer agents to increase the efficiency of transfer of the bioactive therapeutic factor into cells. Suitable transfection enhancer agents include, for example, without limitation, DEAE-dextran, polybrene, lysosome-disruptive peptide, chondroitan-based proteoglycans, sulfated proteoglycans, polyethylenimine, polylysine, integrin-binding peptide CYGGRGDTP, linear dextran nonasaccharide, glycerol, cholesteryl groups tethered at the 3'-terminal internucleoside link of an oligonucleotide, lysophosphatide, lysophosphatidylcholine, lysophosphatidylethanolamine, and 1-oleoyl lysophosphatidylcholine.

In another preferred embodiment of the invention, the construct is a viral vector; it is especially preferred that the viral vector is a retroviral plasmid or an adenovirus.

The term "vector" refers to a nucleic acid molecule capable of transporting another nucleic acid to which it has been linked. The term "expression vector" includes any vector, (e.g., a plasmid, cosmid, phage or artificial chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

Preferably the expression vectors contain a nucleic acid encoding a bioactive therapeutic factor or polypeptide. One type of vector is a "plasmid", which refers to a circular double stranded DNA loop into which additional DNA segments can be ligated. Another type of vector is a viral vector, wherein additional DNA segments can be ligated into the viral genome. Specific examples of viral vectors, include, without limitation, adenovirus and retrovirus vectors for gene therapy using microspheres and transfection agents. Also contemplated within the present invention is the use of a virus-like particle containing a bioactive therapeutic factor, wherein the virus-like particle is physically linked to the transfection agent, which is also linked to the microparticle. Such virus-like particles may be designed using polyethylenimine (PEI) conjugated to a therapeutic sequence. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors comprise a nucleic acid in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, operably linked is intended to mean that the nucleotide sequence of interest is linked to-the regulatory sequence(s) in a manner which allows for expression of the nucleotide sequence (e.g., in an in vitro transcription/translation system or in a host cell when the vector is introduced into the host cell). The term regulatory sequence is intended to include promoters, enhancers and other expression control elements (e.g. polyadenylation or poly T signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells or host organisms to thereby produce proteins or peptides, including fusion proteins or peptides, encoded by nucleic acids as described herein. In addition, the expression vector may comprise additional elements. For example, the expression vector may have two replication systems, thus allowing it to be maintained in two organisms. Furthermore, for integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

The parallel or delayed use of other promoters besides the pol III promoter is of course also possible. The use of a number of different vectors in addition to the use of different promoters can also be preferred or advantageous.

The recombinant expression vectors of the invention can be designed for expression of a polypeptide in eukaryotic cells (e.g., insect cells (using baculovirus expression vectors), yeast cells, or mammalian cells, or in an organism), whereby these cells are usable as drugs or pharmaceutical compositions in gene therapy. Suitable host cells are discussed further in Goeddel, supra.

The term gene therapy construct/expression construct or gene therapy means/expression means are clearly defined for a skilled person in the art (e.g. 20050260576, 20050239069, 20030216337, 20030181377, 20030013136, 20020082410, 20020049176).

In another embodiment, a nucleic acid is expressed in mammalian cells or an organism using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43 235-275), in particular promoters of T cell receptors (Winoto and Baltimore (1989). EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), prostate-specific promoters and/or enhancers (U.S. Pat. Nos. 5,830,686, and 5,871,726, the entire of which are incorporated herein by reference in their entirety) and mammary gland-specific promoters (e.g., milk whey promoter, U.S. Pat. No. 4,873,316 and European Application Publication No. 264,166). Developmentally-regulated promoters are also encompassed, for example the murine hox promoters (Kessel and Gruss (1990) Science 249:374-379) and the alpha-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a given polypeptide.

Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

A specific example would be the use of cancer specific antigen promoter/enhancer to direct a bioactive therapeutic factor of the present invention to the cancer of a patient in need of treatment for cancer. One could also treat specialized cancers by the transfer of genes such as, for example, without limitation, the p53 gene, the retinoblastoma gene (and others of that gene family) that suppress the cancer properties of certain cancers. However, the treatment is applicable not only to cancer but to every other genetic disease.

For the purpose of gene therapy according to the invention, adenoviruses carrying deletions or other vectors have been proposed as suitable vehicles. Adenoviruses are non-enveloped DNA viruses. Gene-transfer vectors derived from adenoviruses (so-called adenoviral vectors) have a number of features that make them particularly useful for gene transfer for such purposes. For example, the biology of the adenoviruses is characterized in detail, the adenovirus is not associated with severe human pathology, the virus is extremely efficient in introducing its DNA into the host cell, the virus can infect a wide variety of cells and has a broad host-range, the virus can be produced in large quantities with relative ease, and the virus can be rendered replication defective by deletions in, inter alia, the early-region 1 of the viral genome.

The adenovirus genome is a linear double-stranded DNA molecule of approximately 36,000 base pairs with the 55-kDa terminal protein covalently bound to the 5' terminus of each DNA strand. The Ad DNA contains identical Inverted Terminal Repeats (ITRs) of about 100 base pairs with the exact length depending on the serotype. The viral origins of replication are located within the ITRs exactly at the genome ends. DNA synthesis occurs in two stages. First, the replication proceeds by strand displacement, generating a daughter duplex molecule and a parental displaced strand. The displaced strand is single-stranded and can form a so-called "panhandle" intermediate, which allows replication initiation and generation of a daughter duplex molecule. Alternatively, replication may proceed from both ends of the genome simultaneously, obviating the requirement to form the panhandle structure.

The term "retrovirus" refers to any known retrovirus (natural and recombinant) (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). "Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (Fly), equine immunodeficiency virus (EIV), and other classes of retroviruses.

Retroviruses are RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions, appears at both the 5' and 3' ends of the viral genome. In one embodiment of the invention, the promoter within the LTR, including the 5' LTR, is replaced with a heterologous promoter. Examples of heterologous promoters which can be used include, for example, the cytomegalovirus (CMV) promoter or Pol III promoter such as U6 or H1.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

As used herein, the term "gene of interest" refers to the gene inserted into an expression vector. In one embodiment, the gene of interest encodes a gene which provides a therapeutic function for the treatment of a genetic disease like cancer or hemoglobinopathy.

The term "gene delivery" or "gene transfer" refers to methods or systems for reliably inserting foreign DNA into target cells, such as into muscle cells or others. Such methods can result in transient or long term expression of genes. Gene transfer provides a unique approach for the treatment of acquired and inherited diseases. A number of systems have been developed for gene transfer into mammalian cells.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian or non-mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

In addition to virus-mediated gene-delivery systems, there are several nonviral options for gene delivery. The simplest method is the direct introduction of therapeutic DNA into target cells. This approach is limited in its application because it can be used only with certain tissues and requires large amounts of DNA.

Another non-viral approach involves the creation of an artificial lipid sphere with an aqueous core. This liposome, which carries the therapeutic DNA, is capable of passing the DNA through the target cell's membrane.

Therapeutic DNA also can get inside target cells by chemically linking the DNA to a molecule that will bind to special cell receptors. Once bound to these receptors, the therapeutic DNA constructs are engulfed by the cell membrane and passed into the interior of the target cell. This delivery system tends to be less effective than other options.

Persons skilled in the art are also experimenting with introducing a $47^{th}$ (artificial human) chromosome into target cells. This chromosome would exist autonomously alongside the standard 46—not affecting their workings or causing any mutations. It would be a large vector capable of carrying substantial amounts of genetic code, and scientists anticipate that, because of its construction and autonomy, the body's immune systems would not attack it. A problem with this potential method is the difficulty in delivering such a large molecule to the nucleus of a target cell.

The invention relates also to procaryotic or eukaryotic cells—in vitro or in vivo (e.g. in an organism)—comprising the construct of the invention or an animal comprising the construct of the invention and/or the cell of the invention.

By "organism" is meant any biological form or thing that is capable of self replication or replication in a host. Examples of "organisms" include the following kinds of organisms (which kinds are not necessarily mutually-exclusive): animals, plants, insects, cyanobacteria, microorganisms, fungi, bacteria, eukaryotes, prokaryotes, mycoplasma, viral organisms (including DNA viruses, RNA viruses), and prions. By animal is meant any mammal including, but not limited to, human, mouse, rat, hamster, cow, pig, horse, sheep, or any mammal or non-mammal.

The invention also relates to a pharmaceutical composition, comprising the gene therapy construct of the invention and a pharmaceutically acceptable carrier.

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention in an effective amount may be dissolved or dispersed in a pharmaceutically acceptable carrier or aqueous medium. Such compositions also are referred to as inocula. The phrase pharmaceutically or pharmacologically acceptable refers to molecular entities and compositions that do not produce adverse, allergic, or other untoward reactions when administered to an animal or a human. As used herein, pharmaceutically acceptable carrier, includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Solutions of the active compounds as free base or pharmacologically acceptable salts can be prepared in water suitably mixed with a surfactant, such as hydroxypropyl-cellulose. Dispersions also can be prepared in glycerol, liquid polyethylene glycols, and mixtures thereof and in oils. Under ordinary conditions of storage and use, these preparations contain a preservative to prevent the growth of microorganisms.

The above-mentioned physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

In addition to the active substance(s), i.e., the composition according to the invention, solutions and emulsions may include conventional carriers such as solvents, solubilizers, and emulsifiers such as water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, peanut oil, corn oil, olive oil, castor oil and sesame oil, glycerol, glycerol formal, tetrahydrofurfuryl alcohol, polyethylene glycols, and fatty esters of sorbitan, or mixtures of these substances. For parenteral application, the solutions and emulsions may also be present in a sterile and blood-isotonic form.

In addition to the active substance(s), suspensions may include conventional carriers such as liquid diluents, e.g. water, ethyl alcohol, propylene glycol, suspending agents, e.g. ethoxylated isostearyl alcohols, polyoxyethylenesorbitol and sorbitan esters, microcrystalline cellulose, aluminum metahydroxide, bentonite, agar, and tragacanth, or mixtures of these substances.

The composition(s) of the present invention may be delivered orally, nasally, intramuscularly, intraperitoneally. In some embodiments, local or regional delivery of pharmaceutical composition, preferably in combination with a second agent (conventional agent), to a patient with e.g. cancer or pre-cancer conditions—or other diseases associated to genetic mutations—will be a very efficient method of delivery to counteract the clinical disease. Similarly, chemo- or radiotherapy may be directed to a particular, affected region of the subject's body. Regional chemotherapy typically involves targeting anti-cancer agents to the region of the body where the cancer cells or tumor are located. Other examples of delivery of the compounds of the present invention that may be employed include intra-arterial, intracavity, intravesical, intrathecal, intrapleural, and intraperitoneal routes.

Intra-arterial administration is achieved using a catheter that is inserted into an artery to an organ or to an extremity. Typically, a pump is attached to the catheter. Intracavity administration describes when chemotherapeutic drugs are introduced directly into a body cavity such as intravesical (into the bladder), peritoneal (abdominal) cavity, or pleural (chest) cavity. Agents can be given directly via catheter. Intravesical chemotherapy involves a urinary catheter to provide drugs to the bladder, and is thus useful for the treatment of bladder cancer. Intrapleural administration is accomplished using large and small chest catheters, while a Tenkhoff catheter (a catheter specially designed for removing or adding large amounts of fluid from or into the peritoneum) or a catheter with an implanted port is used for intraperitoneal chemotherapy. Abdomen cancer or other genetic abdominal diseases may be treated this way. Because most drugs do not penetrate the blood/brain barrier, intrathecal chemotherapy is used to reach cancer cells in the central nervous system. To do this, drugs are administered directly into the cerebrospinal fluid. This method is useful to treat leukemia or cancers that have spread to the spinal cord or brain.

Alternatively, systemic delivery of drugs containing the construct of the invention may be appropriate in certain circumstances, for example, where extensive metastasis has occurred. Chemotherapeutic drugs can also be parallely systematically administered if a patient is being treated with the construct of the invention. Intravenous therapy can be implemented in a number of ways, such as by peripheral access or through a vascular access device; a device that includes a catheter, which is placed into a large vein in the arm, chest, or neck. It can be used to administer several drugs simultaneously, for long-term treatment, for continuous infusion, and for drugs that are vesicants, which may produce serious injury to skin or muscle. Various types of vascular access devices are available.

The therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to well known parameters. Suitable excipients for formulation with deguelin or derivatives thereof in combination a second agent include croscannellose sodium, hydroxypropyl methylcellulose, iron oxides synthetic), magnesium stearate, microcrystalline cellulose, polyethylene glycol 400, polysorbate 80, povidone, silicon dioxide, titanium dioxide, and water (purified).

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray or particle bombardment methods such as gene-gun.

The construct of the present invention may include classic pharmaceutical preparations (e.g. conventional pharmaceutical preparations used in the therapy of genetic diseases or for alleviating the consequences of such diseases). Administration of these compositions according to the present invention will be via any common route so long as the target tissue is available via that route. This includes but is not limited to, oral, nasal, or buccal routes. Alternatively, administration may be by orthotopic, intradermal, subcutaneous, intramuscular, intraperitoneal or intravenous injection. Such compositions would normally be administered as pharmaceutically acceptable compositions, described supra. The drugs and agents also may be administered parenterally or intraperitoneally. The term "parenteral" is generally used to refer to drugs given intravenously, intramuscularly, or subcutaneously.

An effective amount of the therapeutic agent(s) is determined based on the intended goal, for example (i) inhibition of tumor cell proliferation or (ii) elimination of tumor cells. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

Another aspect of the invention is a method for controlled protein expression in vivo or intro, whereby a RNA pol III dependent promoter sequence is used for the protein expression.

In a preferred embodiment, the controlled protein expression comprises a gene therapy. Therapy according to the invention is understood as gene therapy which may however be combined with a simultaneous or delayed conventional therapy. The therapy according to the invention may therefore also consist in more than one therapeutic method (gene therapy with simultaneous conventional therapy). It is preferred that the RNA pol III dependent promoter sequences are selected from the group comprising Human U6, Mouse U6 and/or Human H1. The invention relates also to the use of Pol III promoters or their derivatives for gene therapy and applications related to gene expression for therapeutic purposes. Preferred is the use in applications utilizing their capacity for protein expression.

In the context of the invention, gene therapy is a technique for correcting defective genes responsible for disease development. A person skilled in the art may use one of several approaches for correcting faulty genes: (i) A normal gene may be inserted into a nonspecific location within the genome to replace a nonfunctional gene. This approach is most common. (ii) An abnormal gene could be swapped for a normal gene through homologous recombination. (iii) The abnormal gene could be repaired through selective reverse mutation, which returns the gene to its normal function. (iv) The regulation (the degree to which a gene is turned on or off) of a particular gene could be altered. (v) Therapeutic or advantageous gene can be used to introduce beneficial or new specificity (e.g. T cell receptor introduced to T or stem cell).

In the context of the methods or the uses of the invention, typical subjects to which nucleic acid will be administered for therapeutic application include mammals, particularly primates, especially humans, and subjects for xenotransplant applications such as a primate or swine, especially pigs. For veterinary applications, a wide variety of subjects will be suitable, e.g. livestock such as cattle, sheep, goats, cows, swine and the like; poultry such as chickens, ducks, geese, turkeys and the like; and pets such as dogs and cats. For diagnostic or research applications, a wide variety of mammals will be suitable subjects including rodents (e.g. mice, rats, hamsters), rabbits, primates, and swine such as inbred pigs and the like.

An "expressible" gene is a polynucleotide with an encoding sequence, which is capable of producing the functional form of the encoded molecule in a particular cell. For a sequence encoding a polypeptide, the gene is capable of being transcribed and translated. For an anti-sense molecule, the gene is capable of producing replicate transcripts comprising anti-sense sequence.

For purposes of the methods/uses of the invention (e.g. gene therapy), the vector will typically contain a heterologous polynucleotide of interest containing a region with a beneficial function. The polynucleotide can be directly therapeutic, but more usually will be transcribed into a therapeutic polynucleotide, such as a ribozyme or anti-sense strand, or transcribed and translated into a therapeutic polypeptide. Alternatively or in addition, the polynucleotide can provide a function that is not directly therapeutic, but which permits or facilitates another composition or agent to exert a therapeutic effect. The heterologous polynucleotide, if included, will be of sufficient length to provide the desired function or encoding sequence, and will generally be at least about few (e.g. epitope encoding) to 100 base pairs long, more usually at least about 200 base pairs, frequently at least about 500 base pairs, often at least about 2 kilobases, and on some occasions about 5 kilobases or more.

In the context of the methods/uses of the invention, the effective dose of nucleic acid will be a function of the particular expressed protein, the target tissue, the subject (including species, weight, sex, general health, etc.) and the subject's clinical condition. Optimal administration rates for a given protocol of administration can be readily ascertained by those skilled in the art using conventional dosage determination tests. Additionally, frequency of administration for a given therapy can vary, particularly with the time cells containing the exogenous nucleic acid continue to produce the desired polypeptide as will be appreciated by those skilled in the art. Also, in certain therapies, it may be desirable to employ two or more different proteins to optimize therapeutic results.

The concentration of nucleic acid within a carrier, e.g. a polymer nanoparticle can vary, but relatively high concentrations are preferred to provide increased efficiency of nucleic acid uptake. More specifically, preferred carriers like nanoparticles and micelles comprise a cationic biopolymer-nucleic acid complex particularly optionally substituted cationic chitosan-nucleic acid complexes and includes between about 1% to 70% by weight of the nucleic acid. More preferably, the nanoparticle comprises about 10 to about 60% nucleic acid by weight or 10%, 20%, 30%, 40%, 50% or 60% by weight of the nucleic acid.

In the context of the invention, a drug can be the vector of the invention or a cell which comprises this vector; drug can however also be a conventional drug, administered simultaneously or delayed to the vector according to the invention. Additionally to the construct of the invention, a pharmaceutical composition may also include conventional biologically active substances or further gene constructs.

Non-limiting examples of useful biologically active substances include the following expanded therapeutic categories: anabolic agents, antacids, anti-asthmatic agents, anti-cholesterolemic and anti-lipid agents, anticoagulants, anti-convulsants, anti-diarrheals, antiemetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

Specific examples of useful biologically active substances from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenylpropanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as antifungals, anti-virals, antiseptics and antibiotics; and (o) antigenic materials, particularly those useful in vaccine applications.

Preferably, the biologically active substance is selected from the group consisting of polysaccharides, growth factors, hormones, anti-angiogenesis factors, interferons or cytokines, DNA, RNA, proteins and pro-drugs. In a particularly preferred embodiment, the biologically active substance is a therapeutic drug or pro-drug, more preferably a drug selected from the group consisting of chemotherapeutic agents and other anti-neoplastics, antibiotics, anti-virals, anti-fungals, anti-inflammatories, anticoagulants, an antigenic materials. Particularly preferred biologically active substances are DNA and RNA sequences that are suitable for gene therapy.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

In addition, the compositions of carriers can also comprise additional cationic, anionic and/or neutral biopolymers, so long as they do not interfere undesirably with the biodegradation characteristics of the composition. Mixtures of two or more optionally substituted cationic, anionic and/or neutral polymers may offer even greater flexibility in designing the precise release profile desired for oral administration of the complexed biologically active substance, gene or gene fragment.

The invention also relates to the use of the composition and/or pharmaceutical agent of the invention in the treatment of diseases associated with disorders of genes. These can be autoimmune diseases, and diseases associated with cell division disorders, such as cancer.

Diseases in the meaning of the invention are also diseases entirely or partially due to the formation of autoantibodies and their damaging effect on the overall organism or organ systems, i.e., due to autoaggression. A classification into organ-specific, intermediary and/or systemic autoimmune diseases can be made. Preferred organ-specific autoimmune disease are HASHIMOTO thyroiditis, primary myxedema, thyrotoxicosis (BASEDOW disease), pernicious anemia, ADDISON disease, myasthenia gravis and/or juvenile diabetes mellitus. Preferred intermediary autoimmune diseases are GOODPASTURE syndrome, autoimmune hemolytic anemia, autoimmune leukopenia, idiopathic thrombocytopenia, pemphigus vulgaris, sympathetic ophthalmia, primary bile cirrhosis, autoimmune hepatitis, colitis ulcerosa and/or SJÖGREN syndrome. Preferred systemic autoimmune diseases are rheumatoid arthritis, rheumatic fever, systemic lupus erythematodes, dermatomyositis/polymyositis, progressive systemic sclerosis, WEGENER granulomatosis, panarteritis nodosa and/or hypersensitivity angiitis. Typical autoimmune diseases are thyrotoxicosis, thyroid-caused myxedema, HASHIMOTO thyroiditis, generalized endocrinopathy, pernicious anemia, chronic gastritis type A, diseases of single or all corpuscular elements of the blood (for example, autoimmune hemolytic anemia, idiopathic thrombocytopenia or thrombocytopathy; idiopathic leukopenia or agranulocytosis), pemphigus vulgaris and pemphigoid, sympathetic ophthalmia, and numerous forms of uveitis, primarily biliary liver cirrhosis and chronic aggressive autoimmune hepatitis, diabetes mellitus type I, CROHN disease and colitis ulcerosa, SJÖGREN syndrome, ADDISON disease, lupus erythematodes disseminatus and discoid form of said disease, as dermatomyositis and scleroderma, rheumatoid arthritis (=primarily chronic polyarthritis), antiglomerular basement membrane nephritis. The basis is an aggressive immune reaction due to breakdown of the immune tolerance to self-determinants and a reduction of the activity of T suppressor cells (with lymphocyte marker T8) or an excess of T helper cells (with lymphocyte marker T4) over the suppressor cells; furthermore, formation of autoantigens is possible e.g. by coupling of host proteins to haptens (e.g. drugs), by ontogenetic tissue not developing until self-tolerance has developed, by protein components demasked as a result of conformational changes of proteins in connection with e.g. infection by viruses or bacteria; and by new proteins formed in connection with neoplasias.

Septicemic diseases in the meaning of the invention are diseases due to continuous or periodic invasion of pathogenic bacteria and/or their toxins from a focus of disease and their spreading on the lymph-blood route to form a general or local infection.

Septicemia in the meaning of the invention is preferably wound septicemia (phlegmon, thrombophlebitis, lymphangitis), puerperal septicemia (in case of puerperal fever), otogenic septicemia (in case of otitis media), tonsillogenic septicemia (in case of angina, peritonsillitis), cholangitic septicemia (in case of purulent cholecystitis, cholangitis), pylephlebitic septicemia (in case of pylephlebitis) umbilical septicemia (in case of omphalitis etc.), urosepticemia, as well as dental granuloma. Septicemia in the meaning of the invention can be acute to highly acute (foudroyant), subacute (e.g. as endocarditis lenta) or chronic, and of course, can also be neonatal septicemia.

Therefore, septicemias in the meaning of the invention are all pathogenic changes in a patient which can be associated with intermittent fever and cold chills, with spleen tumor, toxic reactions or damage of the bone marrow or blood (polynuclear leukocytosis, anemia, hemolysis, thrombocytopenia) or with pathogenic reactions in the heart and vasomotor nerve (tachycardia, centralization of the blood circulation, edemas, oliguria; possibly shock) or in the digestive tract (dry, coated tongue, diarrhea), or with septicopyemia (pyemia with formation of septic infarction and metastatic abscess).

In the meaning of the invention, preferred diseases include: AIDS, acne, albuminuria (proteinuria), alcohol withdrawal syndrome, allergies, alopecia (loss of hair), ALS (amyotrophic lateral sclerosis), Alzheimer's disease, retinal macula senile degeneration, anemia, thalassemia, anxiety syndrome, anthrax (milzbrand) aortic sclerosis, occlusive arterial disease, arteriosclerosis, arterial occlusion, arteriitis temporalis, arteriovenous fistula, asthma, respiratory insufficiency, autoimmune disease, prolapsed intervertebral disc, inflammation of the peritoneum, pancreatic cancer, Becker muscular dystrophy, benign prostate hyperplasia (BPH), bladder carcinoma, hemophilia, bronchial carcinoma, breast cancer, BSE, chlamydia infection, chronic pain, cirrhosis, commotio cerebri (brain concussion), Creutzfeld-Jacob disease, intestinal carcinoma, intestinal tuberculosis, depression, diabetes insipidus, diabetes mellitus, diabetes mellitus juvenilis, diabetic retinopathy, Duchenne muscular dystrophia, duodenal carcinoma, dystrophia musculorum progressiva, dystrophia, Ebola, eczema, erectile dysfunction, obesity, fibrosis, cervix cancer, uterine cancer, cerebral hemorrhage, encephalitis, loss of hair, hemiplegia, hemolytic anemia, hemophilia, urinary incontinence, pet allergy (animal hair allergy), skin cancer, herpes zoster, cardiac infarction, cardiac insufficiency, cardiovalvulitis, cerebral metastases, cerebral stroke, cerebral tumor, testicle cancer, ischemia, Kahler's disease (plasmocytoma), polio (poliomyelitis), rarefaction of bone, colon carcinoma, contact eczema, palsy, liver cirrhosis, leukemia, pulmonary fibrosis, lung cancer, pulmonary edema, lymph node cancer, (Morbus Hodgkin), lymphogranulomatosis, lymphoma, lyssa, gastric carcinoma, meningitis, mucoviscidosis (cystic fibrosis), multiple sclerosis (MS), myocardial infarction, neurodermitis, neurofibromatosis, neuronal tumors, kidney cancer (kidney cell carcinoma), osteoporosis, pancreas carcinoma, pneumonia, polyarthritis, polyneuropathies, potency disorders, progressive systemic sclerosi (PSS), prostate cancer, rectum carcinoma, pleurisy, craniocerebral trauma, vaginal carcinoma, sinusitis, esophagus cancer, tremor, tuberculosis, tumor pain, burns/scalds, intoxications, viral meningitis, menopause, soft-tissue sarcoma, soft-tissue tumor, cerebral blood circulation disorders, CNS tumors.

In a preferred embodiment the cancerous disease or tumor being treated or prevented is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchioalveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lympharigioma, lymphangiomyoma, lymphangiosarcoma; pinealoma; cystosarcoma phylloides; hemangiosarcoma; lymphangiosarcoma; myxosarcoma, ovarial carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In another preferred embodiment the cancerous disease or tumor being treated or prevented is selected from the group of tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarial carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, morbus Hodgkin, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancy such as Kaposi sarcoma, AIDS-associated lymphomas, AIDS-associated lymphomas of the central nervous system, AIDS-associated morbus Hodgkin and AIDS-associated anogenital tumors, transplantation-related malignancy, metastasized tumors comprising brain metastases, lung metastases, liver metastases, bone metastases, pleural and pericardial metastases, and malignant ascites.

In another preferred embodiment the cancerous disease or tumor being treated or prevented is selected from the group comprising mammary carcinomas, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

The invention relates also to a therapeutic gene expression system, which is not associated aberrant expression of adjacent gene or the risk of changing the pattern of gene expression profile.

The invention is further illustrated by the following examples which should not be construed as limiting:

Cell Lines and Clones

Cryopreserved PBMC were collected from healthy donor blood donation by centrifugation on Ficoll-Hypaque gradients as by the manufacturer procedures. PBMC were stimulated with 10 ng/ml CD3 (ORTHOCLONE OKT3, Ortho Biotech, Bridgewater, N.J.) and 600 IU IL-2/ml (13). Three days later cells were transduced as described below. Transduced T cells were cultured in complete medium (CM; RPMI 1640 supplemented with 10% FBS, L-Glu, 50 mM b-mercaptoethanol and antibiotics, all from Gibco, Invitrogen, Karlsruhe, Germany), containing 300 IU human IL-2/ml (CM-2).

Plasmid and Retroviral Constructs

Retroviral construct based on the modified mouse stem-cell virus (MSCV) system pSuper-retro neo-GFP (11) was purchased from Oligoengine (Seattle, Wash.). It contains H1 a type III pol III promoter. Puromycin-containing vectors originated from the pSuper-retro neo-GFP plasmid. They differed in their antibiotic resistance gene and by including another pol III promoter, U6, which was obtained from vector pSilencer U6 (Ambion, Cambridgeshire, UK) after shuttling it in Litmus 28 vector from New England Biolabs (Frankfurt am Main, Germany). The neomycin resistance gene (neo$^r$) plus a part of the PGK promoter were excised with Nsi I and Blp I and replaced by puromycin resistance gene (puro$^r$) plus the same Nsi I-Blp I fragment of the PGK promoter, which was excised from the MSCV vector (Clontech, Heidelberg, Germany). For constructing 30, pSuper-U6-GFP the GFP gene (from plasmid pCLEX kindly provided by Dr. W. Uckert) was cloned down stream of the U6 promoter of the pSuper-Puro-U6 plasmid. pSuper-H1-GFP was cloned by deleting the 06 promoter of the pSuper-U6-GFP plasmid. Stop cassettes (sequences indicated in table 1) for the pol III promoters were synthesized at TIB MOL-BIOL (Berlin, Germany) and cloned into the pSuper-U6-GFP plasmid to produce pSuper-U6-STOP-GFP, pSuper-U6-STOP 9-GFP and pSuper-U6-STOP 12-GFP plasmids. pSuper-U6-hRLuc-STOP-GFP, pSuper-U6-hRLuc-STOP-GFP, pSuper-U6-hRLuc-STOP9-GFP expressing the humanized Renilla luciferase (hRLuc) gene were constructed by cloning the hRLuc obtained from the hRLuc-Null plasmid (Promega, Mannheim, Germany) gene down stream of the U6 promoter and upstream of the stop cassettes in the corresponding pSuper-U6-STOP-GFP pSuper-U6-STOP 9-GFP pSuper-U6-STOP 12-GFP plasmids.

Site Directed Mutagenesis

Site directed mutagenesis was performed using the QuickChange II kite from Stratagene (La Jolla, Calif.) and mutagenizing oligos (Table 1) were synthesized at TIB MOL-BIOL. Mutations were confirmed by sequencing (Invitek, Berlin).

Tumor Cells

HEK-T, Jurkat, NIH-3T3 (kindly provided by Dr. W. Uckert, MDC, Berlin) and Plat-E cells (kindly provided by Dr. T. Kitamura, University of Tokyo, Tokyo) were cultured in a humidified atmosphere at 37° C. and 8% CO2 incubator in CM.

Cell Transfection and Retrovirus Production

Retroviruses that were used for transduction of murine cells were produced by Plat-E packaging cells, whereas retroviruses that were used for transduction of human cells (Jurkat or PBL derived T cells) were produced by co-transfecting HEK-T cells with the construct of interest plus the pCL-10A1 encoding the 10A1 envelope gene (kindly provided by Dr. P. F. Robbins, NCI, NIH, Bethesda, Md.). Lipofectaminm 2000 (Invitrogen, Karlsruhe, Germany) was used for the transfection using 10 µl of Lipofectamine and 3 µg of the plasmid (1.5 µg of each plasmid when two plasmids were used for the co-transfection) in a well of 6-well plate as per the manufacturer procedures. The cells were transfected over night and the medium was replaced by CM on the next day. For optimal virus production the cells were cultured at 32° C. for 3 days.

Cell Transduction and Virus Titer Determination

Two rounds of T cell transduction were performed as previously described (13). One week later the percentage of the transduced cells was estimated by FACS analysis based on GFP expression using a FACScan (BD, San Jose, Calif.). NIH 3T3 or HEK-T cells were used as target cells for the determination of the virus titer. $2 \times 10^3$ cells were plated into wells of a 24-well plate one day prior to transduction. After 24 hr the medium was exchanged and 900 µl of fresh CM was added. Serially diluted (1:10) virus containing supernatants including polybrene (8-10 µg/ml) were then added to the cells. This was followed by spin-infection for 1 hr at 30° C. and 2500 rpm. After centrifugation the cells were cultured over night and the retrovirus-containing medium was replaced by 1 ml of fresh CM on the next day. Three days later those cells that had been transduced with the GFP/Neo containing viruses were trypsinized and analyzed by flow cytometry. The virus titer was calculated as earlier described (14).

Luminescence Measurement

Luminescence was measured by using either the Aequoria imaging system (Hamamatsu Photonic, Herrsching am Ammersee, Germany) or Mithras LB 940 luminometer (Berthold Technologies, Berlin, Germany). Coelenterazine was added at a concentration of 5 mg per ml and cultures were imaged directly after adding the substrate for 10 seconds with the luminometer or for 1 minute with the imaging system.

TABLE 1

List of Human and *S. cerevisiae* Pol II subunits

| Subunit | Mass, kDa | Saccharomyces cerevisiae |
|---|---|---|
| hRPB1 | 220 | B220 |
| hRPB2 | 140 | B150 |
| hRPB3 | 33 | B44 |
| hRPB4 | 16.3 | B32 |
| hRPB5 | 25 | ABC27 |
| hRPB6 | 14.4 | ABC23 |
| hRPB7 | 19 | B16 |
| hRPB8 | 17 | ABC14.5 |
| hRPB9 | 14.5 | B12.6 |
| hRPB10α | 7.0 | ABC10α |

TABLE 1-continued

List of Human and *S. cerevisiae* Pol II subunits

| Subunit | Mass, kDa | Saccharomyces cerevisiae |
|---|---|---|
| hRPB10β | 7.6 | ABC10β |
| hRPB11 | 14 | B12.5 |

Adapted from Schlegel B P, Green V J, Ladias J A, Parvin J D. BRCA1 interaction with RNA polymerase II reveals a role for hRPB2 and hRPB10alpha in activated transcription. Proc Natl Acad Sci USA. 2000 Mar. 28; 97(7): 3148-53.

TABLE 2

List of pol III subunits of *S. cerevisiae* and human

| S. cerevisiae Subunit | Human homolog Subunit | Relationship to pols |
|---|---|---|
| C160 | hRPC155 | Conserved I, II, III |
| C128 | nd | Conserved I, II, III |
| C82 | hRPC62 | Specific |
| AC40 | hRPC40 | Shared I, III |
| C53 | BN51 | Specific |
| C37 | nd | Specific |
| C34 | hRPC39 | Specific |
| C31 | hRPC32 | Specific |
| ABC23 | hRPC15 | Shared I, II, III |
| ABC27 | hRPC25 | Shared I, II, III |
| C25 | nd | Conserved II, III |
| AC19 | hRPC16 | Shared I, III |
| ABC14.5 | hRPC14 | Shared I, II, III |
| C11 | hRPC11 | Conserved I, II, III |
| ABC10α | hRPC10 | Shared I, II, III |
| ABC10β | hRPC8 | Shared I, II, III |
| C17 | hRPC17 | Specific | nd, not determined.
Adapted from: Huang Y, Maraia R J. Comparison of the RNA polymerase III transcription machinery in *Schizosaccharomyces pombe*, *Saccharomyces cerevisiae* and human. Nucleic Acids Res. 2001 Jul.; 29(13): 2675-90.

The invention claimed is:

1. A gene therapy construct for the expression of protein encoding genes comprising a vector comprising a promoter, wherein the promoter consists of a type 3 RNA pol III dependent promoter, wherein the promoter is operably linked to at least one polynucleotide sequence of interest, wherein the at least one polynucleotide sequence of interest is an expressible protein encoding gene which is transcribed and translated, and at least one RNA pol III dependent transcription termination sequence consisting of a cluster of four or more T residues.

2. The gene therapy construct according to claim 1, wherein the vector is a viral vector.

3. The gene therapy construct according to claim 2, wherein the viral vector is a retroviral vector or adenoviral vector.

4. An isolated eukaryotic cell comprising the construct of claim 1.

5. A pharmaceutical composition comprising the gene therapy construct according to claim 1 and a pharmaceutically acceptable carrier.

6. The gene therapy construct according to claim 1, wherein the type III RNA pol III dependent promoter is a naturally occurring promoter.

7. The gene therapy construct according to claim 1, wherein the polynucleotide sequence of interest encodes a therapeutic protein.

8. The gene therapy construct according to claim 1, wherein the polynucleotide sequence is at least about 200 bps long.

* * * * *